United States Patent
Ghigo et al.

(10) Patent No.: US 7,485,620 B2
(45) Date of Patent: Feb. 3, 2009

(54) PHARMACEUTICAL COMPOSITIONS COMPRISING UNACYLATED GHRELIN AND THERAPEUTICAL USES THEREOF

(75) Inventors: Ezio Ghigo, Turin (IT); Aart Jan Van Der Lely, Bergschenhoek (NL)

(73) Assignee: Alizé Pharma SAS, Ste-Foy-Les-Lyon (FR)

( * ) Notice: Subject to any disclaimer, the term of this patent is extended or adjusted under 35 U.S.C. 154(b) by 259 days.

(21) Appl. No.: 10/499,376

(22) PCT Filed: Dec. 18, 2002

(86) PCT No.: PCT/CA02/01964

§ 371 (c)(1),
(2), (4) Date: Nov. 29, 2004

(87) PCT Pub. No.: WO03/051389

PCT Pub. Date: Jun. 26, 2003

(65) Prior Publication Data

US 2005/0080007 A1    Apr. 14, 2005

(30) Foreign Application Priority Data

Dec. 18, 2001  (CA) ................................. 2365704

(51) Int. Cl.
*A61K 38/00* (2006.01)
(52) U.S. Cl. .................... 514/12; 530/300; 530/308
(58) Field of Classification Search ................. None
See application file for complete search history.

(56) References Cited

FOREIGN PATENT DOCUMENTS

| CA | 2470235 | 6/2003 |
|---|---|---|
| CA | 2471879 | 11/2003 |
| CA | 2543507 | 5/2005 |
| WO | WO-0156592 | 8/2001 |
| WO | WO 01/87335 A2 | 11/2001 |

OTHER PUBLICATIONS

Mickle et al., Med. Clin. North Am., 2000, vol. 84(3), p. 597-607.*
Adelhorst et al., J. Biol. Chem. 269: 6275-6278, 1994.*
Marzullo et al., J. Clin. Endocr. Metab. 89: 936-939, 2004.*
Cassoni, Paola et al., "Identification, Characterization, and Biological Activity of Specific Receptors for Natural Ghrelin) and Synthetic Growth Hormone Secretagogues and Analogs in Human Breast Carcinomas and Cell Lines," *The Journal of Clinical Endocrinology & Metabolism* 86(4): 1738-1744 (2001).
Toshinai, Koji et al., "Upregulation of Ghrelin Expression in the Stomach upon Fasting, Insulin-Induced Hypoglycemia, and Leptin Administration," *Biochemical and Biophysical Research Communications* 281: 1220-1225 (2001).
Broglio, et al., Non-Acylated Ghrelin Counteracts the Metabolic but not the Neuroendocrine Response to Acylated Ghrelin in Humans, The Journal of Clinical Endocrinology & Metabolish, vol. 89, No. 6, pp. 3062-3065, Jun. 2004.
Pöykkö, et al., Low Plasma Ghrelin is Associated With Insulin Resistance, Hypertension, and the Prevalence of Type 2 Diabetes, Diabetes, vol. 52, pp. 2546-2553, Oct. 2003.
Granata, et al., Acylated and Unacylated Ghrelin Promote Proliferaion and Inhibit Apoptosis of Pancreatic beta Cells and Human Islets: Involvement of 3', 5'—Cyclic Adenosine Monophosphate/Protein Kinase A, Extracellular Signal-Regulated kinase 1/2, and Phosphatidyl Inositol 3-Kinase/Akt Signaling, Endocrinology, vol. 148, No. 2, pp. 512-529, 2007.
Granata, et al., Acylated and unacylate ghrelin proliferation and inhibit serum stravation- and cytokine-induced apoptosis of pancreatic beta cells through cAMP/PKA, ERK 1/2 and P13K/Akt, Abstract and poster presented at Meeting of the Endocrine Society, Boston, from Jun. 24, 2006.
Prodam, et al., Unacylated Ghrelin (UAG) Enhances the Early Insulin Response to Meal, Improves Glucose Metabolism and Decrease Free Faty Acids Levels in Health Volumteers, Abstract and poster presented at European Congress of Endocrinology, Budapest, from Apr. 28, 2007 to May 2, 2007.

* cited by examiner

*Primary Examiner*—Robert Landsman
*Assistant Examiner*—Gyan Chandra
(74) *Attorney, Agent, or Firm*—Darby & Darby P.C.

(57) ABSTRACT

The present invention relates to compositions containing unacylated ghrelin and derivatives thereof and their uses in the control of glycemia in ageing patients, GH deficient patients, diabetic patients and obese patients.

21 Claims, 5 Drawing Sheets

SEQUENCE LISTING

<160> NUMBER OF SEQ ID NOS: 1

<210> SEQ ID NO 1

<211> LENGTH: 28

<212> TYPE: PRT

<213> ORGANISM: Artificial sequence

<220> FEATURE:

<223> OTHER INFORMATION: synthetic polypeptide: unacylated ghrelin

```
<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

PHARMACEUTICAL COMPOSITIONS COMPRISING UNACYLATED GHRELIN AND THERAPEUTICAL USES THEREOF

CROSS REFERENCE TO RELATED APPLICATION

This application is the 371 National Phase of International Application No. PCT/CA02/01964, filed Dec. 18, 2002, which was published in English under PCT Article 21(2) as International Publication No. WO 03/051389, which is incorporated hereby by reference in its entirety.

BACKGROUND OF THE INVENTION (a) Field of the Invention

This invention relates new compositions comprising unacylalted ghrelin and their therapeutical uses thereof.

(b) Description of Prior Art

Ghrelin is a recently discovered gastric hormone of 28 amino acids showing a unique structure with an n-octanoyl ester at its third serine residue (Kojima M et al. *Nature* 1999; 402(6762):656-660). Though many synthetic peptidyl and nonpeptidyl growth hormone (GH) secretagogues (GHS) were identified as ligands of GHS-R, ghrelin is shown to be a physiological ligand for the GHS-R. Ghrelin powerfully stimulates GH secretion through its interaction with GHS-R both in animals and in humans (Ukkola, O et al., 2002 *Ann. Med.* 34:102-108). The GH-releasing activity of ghrelin is mediated by activation of GHS-R at the pituitary and, mainly, at the hypothalamic level (Kojima M et al. *Nature* 1999; 402(6762):656-660) likely by enhancing the activity of growth hormone releasing hormone (GHRH)-secreting neurons and, concomitantly, acting as a functional somatostatin (SS) antagonist (Ghigo E et al. *Eur J Endocrinol* 1997; 136 (5):445-460). Other mechanisms have been postulated recently as well (Ahnfelt-Ronne I et al. *Endocrine* 2001; 14(1):133-135). The interplay among various factors leading to GH secretion is depicted in FIG. 1.

The GHS-R and its subtypes are not restricted to the hypothalamus-pituitary unit but are present also in other central and peripheral tissues (Papotti M et al. *J Clin Endocrinol Metab* 2000; 85(10):3803-3807) and the physiological actions of ghrelin, as well as those of synthetic GHS are not restricted to GH secretion. In fact, ghrelin stimulates lactotroph and corticotroph hormone secretion, has orexigenic and cardiovascular actions, shows anti proliferative effects on thyroid and breast tumors and regulates gastric motility and acid secretion through vagal mediation (Ukkola, O et al., 2002, *Ann. Med.* 34:102-108).

In humans, fasting leads to elevated serum GH concentrations. Traditionally, changes in hypothalamic GHRH and somatostatin have been considered as the main mechanisms, which induce elevations in GH secretion during fasting. As ghrelin administration in man also stimulates GH release, and serum ghrelin concentrations are elevated during fasting, increased ghrelin actions might be another mechanism whereby fasting results in the stimulation of GH release.

Although ghrelin is likely to regulate pituitary GH secretion in interplay with GHRH and SS, GHS receptors have also been identified on hypothalamic neurons and in the brainstem (Nakazato M et al. *Nature* 2001; 409(6817):194-198). Apart from potential paracrine effects, ghrelin may thus offer an endocrine link between the stomach, hypothalamus and pituitary, suggesting an involvement in the regulation of energy balance. Tschop et al. have shown that daily peripheral administration of ghrelin in mice and rats caused weight gain by reducing fat utilization (Tschop M et al. *Nature* 2000; 19; 407(6806):908-913). Intracerebroventricular administration of ghrelin generated a dosedependent increase in food intake and body weight. Rat serum ghrelin concentrations increased by fasting and decreased by re-feeding or oral glucose administration, but not by water ingestion. Apparently ghrelin, in addition to its role in regulating GH secretion, signals the hypothalamus when an increase in metabolic efficiency is necessary (Tschop M et al. *Nature* 2000; 19; 407(6806):908-913; Muller A F et al. *Clin Endocrinol (Oxf)* 2001; 55(4):461-467).

Studies by Kojima and others have shown that unacylated ghrelin (UAG) has no affinity to the known GHS-R (GHS-R1a receptor), which is responsible for GH release from the pituitary gland (Kojima M et al. *Nature* 1999; 402(6762):656-660). This was confirmed later by Bednarek M A et al (Bednarek M A et al, *J. Med Chem.* 2000, 43:4370-4376), who showed that unacylated ghrelin could not be a physiological ligand of the GHS-R1a receptor (IC50>10,000 nM), since it poorly activated GHS-R1a at micromolar concentrations; large hydrophobic acyl group is obligatory at position 3 of ghrelin for its biological response on GH secretion.

The PCT application, WO 01/87335A2, discloses methods of selectively inhibiting ghrelin actions including those on obesity using growth hormone secretagogue receptor antagonists and ghrelin neutralizing reagents. The ghrelin neutralizing reagents are antibodies, single chain antibodies, antibody fragments, or antibody-based constructs.

Specific binding of acylated ghrelin can be found in many peripheral tissues (Papotti M et al. *J Clin Endocrinol Metab* 2000; 85(10):3803-3807). In these tissues, no mRNA expression of the GHS-R1a receptor could be found, indicating that other receptor (sub)types of receptors that can bind GHS would be responsible for this specific binding. These novel receptor/s may mediate ghrelin's peripheral actions which are, as shown in this invention, efficiently antagonized by unacylated ghrelin.

It would be highly desirable to be provided with pharmaceutical compositions of nonacylated ghrelin for glycemic control in certain metabolic diseases.

SUMMARY OF THE INVENTION

In accordance with the present invention there is provided a composition for preventing and/or reducing postprandial induction of insulin resistance comprising a therapeutically effective amount of at least one of unacylated ghrelin, an analog thereof and a pharmaceutically acceptable salt thereof in association with a pharmaceutically acceptable carrier.

The composition in accordance with a preferred embodiment of the present invention, wherein the unacylated ghrelin is having an amino acid as set forth in SEQ ID NO:1.

In accordance with the present invention, there is provided a method for reducing postprandial induction of insulin resistance in a patient comprising the step of administering a therapeutically effective amount of the composition of the present invention to the patient.

The method in accordance with a preferred embodiment of the present invention, wherein the administration is through a route selected from the group consisting of intravenous, subcutaneous, transdermal, oral, buccal, sublingual, nasal and by inhalation.

The method in accordance with a preferred embodiment of the present invention, wherein the composition is administered in a dose varying from about 0.001 μg/kg to 10.0 μg/kg, more preferably 1 μg/kg to 1 mg/kg.

In accordance with the present invention, there is provided the use of the composition of the present invention for reducing postprandial induction of insulin resistance in a patient.

In accordance with the present invention, there is provided the use of the composition of the present invention for the preparation of a medicament for reducing postprandial induction of insulin resistance in a patient.

In accordance with the present invention, there is provided a composition for preventing and/or reducing dawn phenomenon in type I diabetes patient comprising a therapeutically effective amount of at least one of unacylated ghrelin, an analog thereof and a pharmaceutically acceptable salt thereof in association with a pharmaceutically acceptable carrier.

In accordance with the present invention, there is provided a method for preventing and/or reducing dawn phenomenon in type I diabetes patient comprising the step of administering a therapeutically effective amount of the composition of the present invention to the patient.

In accordance with the present invention, there is provided the use of the composition of the present invention for preventing and/or reducing dawn phenomenon in type I diabetes patient.

In accordance with the present invention, there is provided the use of the composition of the present invention for the preparation of a medicament for preventing and/or reducing dawn phenomenon in type I diabetes patient.

In accordance with the present invention, there is provided a composition for reducing body weight increased in a patient suffering from at least one of type II diabetes and syndrome X comprising a therapeutically effective amount of at least one of unacylated ghrelin, an analog thereof, and a pharmaceutically acceptable salt thereof in association with a pharmaceutically acceptable carrier.

The composition in accordance with a preferred embodiment of the present invention, wherein the patient is treated with oral antidiabetic drugs.

In accordance with the present invention, there is provided a method for reducing a body weight increased encountered by a patient suffering from at least one of type II diabetes and syndrome X comprising the step of administering a therapeutically effective amount of the composition of the present invention.

In accordance with the present invention, there is provided the use of the composition of the present invention for reducing a body weight increased encountered by a patient suffering from at least one of type II diabetes and syndrome X.

In accordance with the present invention, there is provided the use of the composition of the present invention for the preparation of a medicament for reducing a body weight increased encountered by a patient suffering from at least one of type II diabetes and syndrome X.

In accordance with the present invention, there is provided a composition for facilitating treatment of an insulin-resistant patient comprising a therapeutically effective amount of at least one of unacylated ghrelin, an analog thereof and a pharmaceutically acceptable salt thereof in association with a pharmaceutically acceptable carrier.

In accordance with the present invention, there is provided a method for facilitating the treatment of an insulin-resistant patient comprising the step of administering a therapeutically effective amount of the composition of the present invention to the patient.

In accordance with the present invention, there is provided the use of the composition of the present invention for facilitating the treatment of an insulin-resistant patient.

In accordance with the present invention, there is provided the use of the composition of the present invention for the preparation of a medicament for facilitating treatment of insulin-resistant patient.

In accordance with the present invention, there is provided a composition for decreasing fat mass in a growth hormone-deficient patent comprising a therapeutically effective amount of at least one of unacylated ghrelin, an analog thereof and a pharmaceutically acceptable salt thereof in association with a pharmaceutically acceptable carrier.

In accordance with the present invention, there is provided a method for decreasing fat mass in a growth hormone-deficient patient comprising the step of administering a therapeutically effective amount of the composition of the present invention to the patent.

In accordance with the present invention, there is provided the use of the composition of the present invention for decreasing fat mass in a growth hormone-deficient patient.

In accordance with the present invention, there is provided the use of the composition of the present invention for the preparation of a medicament for decreasing fat mass in a growth hormone-deficient patient.

In accordance with the present invention, there is provided a composition for decreasing fat mass in an ageing patient having a high body mass index comprising a therapeutically effective amount of at least one of unacylated ghrelin, an analog thereof and a pharmaceutically acceptable salt thereof in association with a pharmaceutically acceptable carrier.

In accordance with the present invention, there is provided a method for decreasing fat mass in an ageing patent having a high body mass index comprising the step of administering a therapeutically effective amount of the composition of the present invention to the patent.

In accordance with the present invention, there is provided the use of the composition of the present invention for decreasing fat mass in an ageing patient having a high body mass index.

In accordance with the present invention, there is provided the use of the composition of the present invention for the preparation of a medicament for decreasing fat mass in an ageing patient having a high body mass index.

In accordance with the present invention, there is provided a composition for preventing and/or reducing insulin resistance in a patient comprising a therapeutically effective amount of at least one of unacylated ghrelin, an analog thereof and a pharmaceutically acceptable salt thereof in association with a pharmaceutically acceptable carrier.

In accordance with the present invention, there is provided a method for preventing and/or reducing insulin resistance in a patent in severe catabolism comprising the step of administering to said patient a therapeutically effective amount of the composition of the present invention.

In accordance with the present invention, there is provided the use of the composition of the present invention for preventing and/or reducing insulin resistance in a patient in severe catabolism.

In accordance with the present invention, there is provided the use of the composition of the present invention for the preparation of a medicament for preventing and/or reducing insulin resistance in a patient in severe catabolism.

In the present application, the terms "Ghrelin" and "Acylated ghrelin" are used interchangeably and are intended to mean the same.

For the purpose of the present invention the following terms are defined below.

The term "Unacylated ghrelin" is intended to mean peptides that contain the amino acid sequence specified in Seq ID No. 1. Naturally-occuring variations of unacylated ghrelin include peptides that contain substitutions, additions or deletions of one or more amino acids which result due to discrete changes in the nucleotide sequence of the encoding ghrelin gene or its alleles thereof or due to alternative splicing of the transcribed RNA. It is understood that the said changes do not substantially affect the antagonistic properties, pharmacological and biological characteristics of unacylated ghrelin variant. Those peptides may be in the form of salts, particularly the acidic functions of the molecule may be replaced by a salt derivative thereof such as a trifuoroacetate salt.

The term "Analogue of unacylated ghrelin" refers to both structural and functional analogues of unacylated ghrelin which are capable of replacing unacylated ghrelin in antagonizing the peripheral actions of ghrelin. Simple structural analogues comprise peptides showing homology with unacylated ghrelin as set forth in SEQ ID No. 1 or a fragment thereof. For example, an isoform of ghrelin-28 (SEQ ID No. 1), des Gln-14 Ghrelin (a 27 amino acid peptide possessing serine 3 modification by n-octanoic acid) is shown to be present in stomach; it is functionally identical to ghrelin in that it binds to GHS-R1a with similar binding affinity, elicits $Ca^{2+}$ fluxes in cloned cells and induces GH secretion with similar potency as Ghrelin-28.

The term "Homology" refers to sequence similarity between two peptides while retaining an equivalent biological activity. Homology can be determined by comparing each position in the aligned sequences. A degree of homology between amino acid sequences is a function of the number of identical or matching amino acids at positions shared by the sequences so that an "homologous sequence" refers to a sequence sharing homology and an equivalent function or biological activity.

It is known that des-Gln14-ghrelin is a structural analogue and a functional analogue of ghrelin; as such, unacylated des-gln14ghrelin could potentially antagonize effects of ghrelin and des-Gln14-ghrelin on peripheral metabolism involving insulin secretion and glycemic control.

Functional analogues of unacylated ghrelin dispite their diversity have the common interesting property of being able to fully replace unacylated ghrelin in one or more biological activities exhibited by unacylated ghrelin. For example, these biological activities of unacylated ghrelin may include, binding to a specific receptor, altering the signals arising from the activation of said receptor, modulating the functional consequences of activation of said receptor.

Functional analogues of unacylated ghrelin, as well as those of unacylated des-Gln14-ghrelin, are able to produce the biological effects of unacylated ghrelin in antagonizing the peripheral metabolic actions of ghrelin such as those on insulin levels and glycemic control, as described in the present application, hence such functional analogues will be usefull for realizing therapeutic benefits in medical conditions involving GH-deficient states.

Conservative substitutions of one or more amino acids in the primary sequence of unacylated ghrelin may provide structural analogues of the peptide. In order to derive more potent analogues, it is customary to use alanine scans, selective substitutions with D-amino acid or synthetic amino acids, truncation of the peptide sequence in order to find a "functional core" of the peptide, covalent addition of molecules to improve the properties of the peptide such as its serum stability, in vivo half life, potency, hydrophilicity or hydrophobicity and immunogenicity.

General methods and synthetic strategies used in providing functional and structural analogues of peptides is described in publications such as "Solid phase peptide synthesis" by Stewart and Young, W. H. Freeman & Co., San Francisco, 1969 and Erickson and Merrifield, "The Proteins" Vol. 2, p. 255 et seq. (Ed. Neurath and Hill), Academic Press, New York, 1976.

All references herein are hereby incorporated by reference.

DETAILED DESCRIPTION OF THE INVENTION

In accordance with the present invention, there is provided pharmaceutical compositions for acting on insulin levels and glycemia in metabolic diseases.

Figure 1:
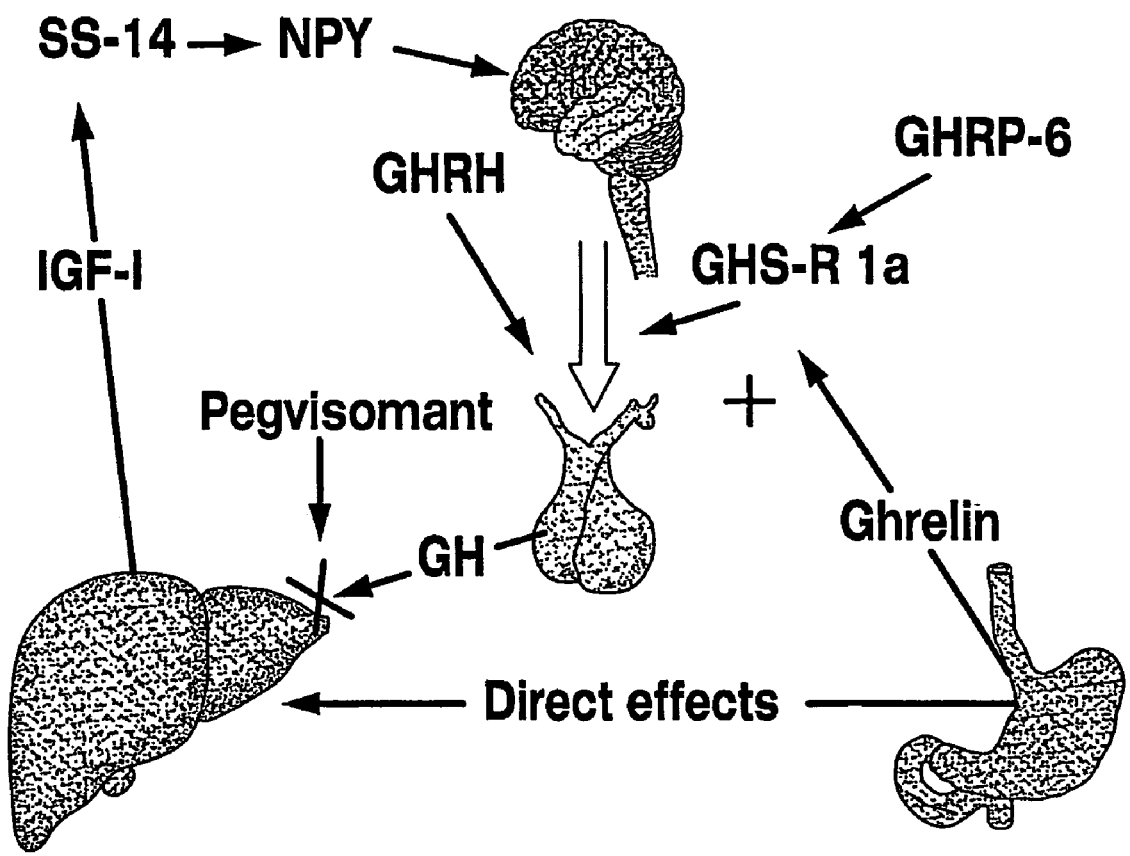
FIG. 1 illustrates the interplay among various factors leading to GH secretion.
Figure 2A:
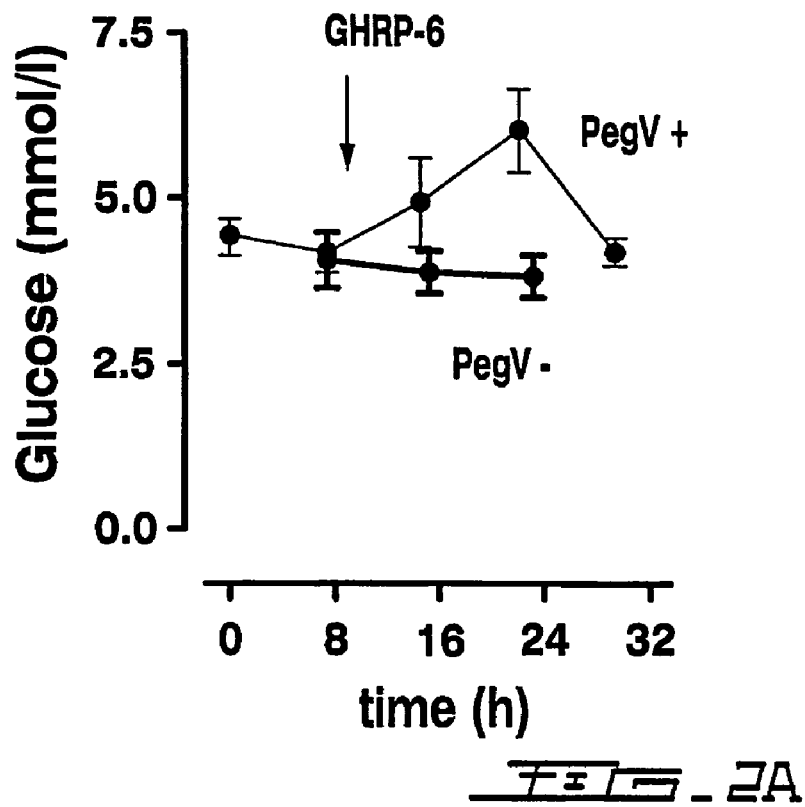
FIG. 2A illustrates glucose concentration over time in absence and in presence of the GH receptor antagonist pegvisomant upon administration of GHRP-6.
Figure 2B:
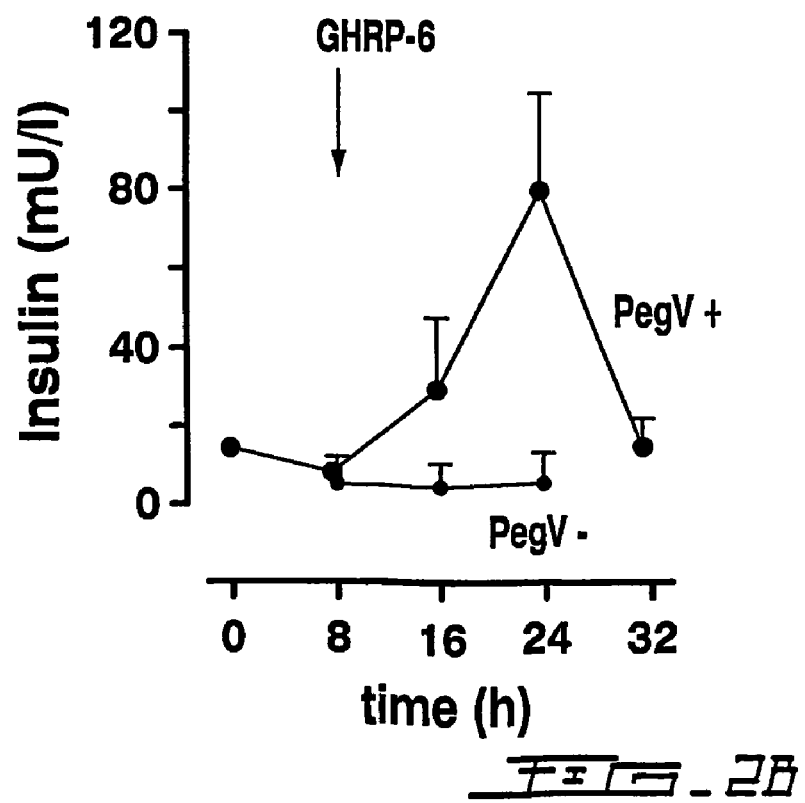
FIG. 2B illustrates insulin concentration over time in absence and in presence of the GH receptor antagonist pegvisomant upon administration of GHRP-6.

It has recently been demonstrated that the growth hormone secretagogue, GHRP-6, has direct and non-GH dependent actions on metabolism (Muller A F et al. *J Clin Endocrinol Metab* 2001; 86(2):590-593). It is shown in the present application that in normal human beings, preprandial GHS administration (1 µg/Kg i.v.) induces a postprandial increase in serum glucose levels, but only in the presence of the GH receptor antagonist pegvisomant (FIG. 2: left panel).

Moreover, this is accompanied by an impressive increase in serum insulin concentrations (indicating insulin resistance; FIG. 2A), and a rapid decrease of free fatty acids. These GHS-mediated changes indicate that when GH bioactivity is lowered (as seen in GH deficient, ageing. obese and diabetic individuals), GHS can induce potent changes in metabolic control, which are characteristic of the "metabolic syndrome X". Because in this study GH-action was blocked by pegvisomant, these GHS-mediated metabolic changes on the "gastro-entero-hepatic axis" must be direct and non-pituitary mediated. Supporting this hypothesis, daily ghrelin administration in rodents for only several days, indeed induces an obese state, again indicating that these GHS-mediated effects on metabolism are powerful and clinically relevant.

The data presented in the present application indicate that GHS-mediated effects are involved in the induction of the metabolic alterations, as well as subsequent changes in body composition, which are characteristic for the insulin resistance syndrome (metabolic syndrome), as observed in GH deficiency, but also during normal ageing, obesity and diabetes.

Figure 3:
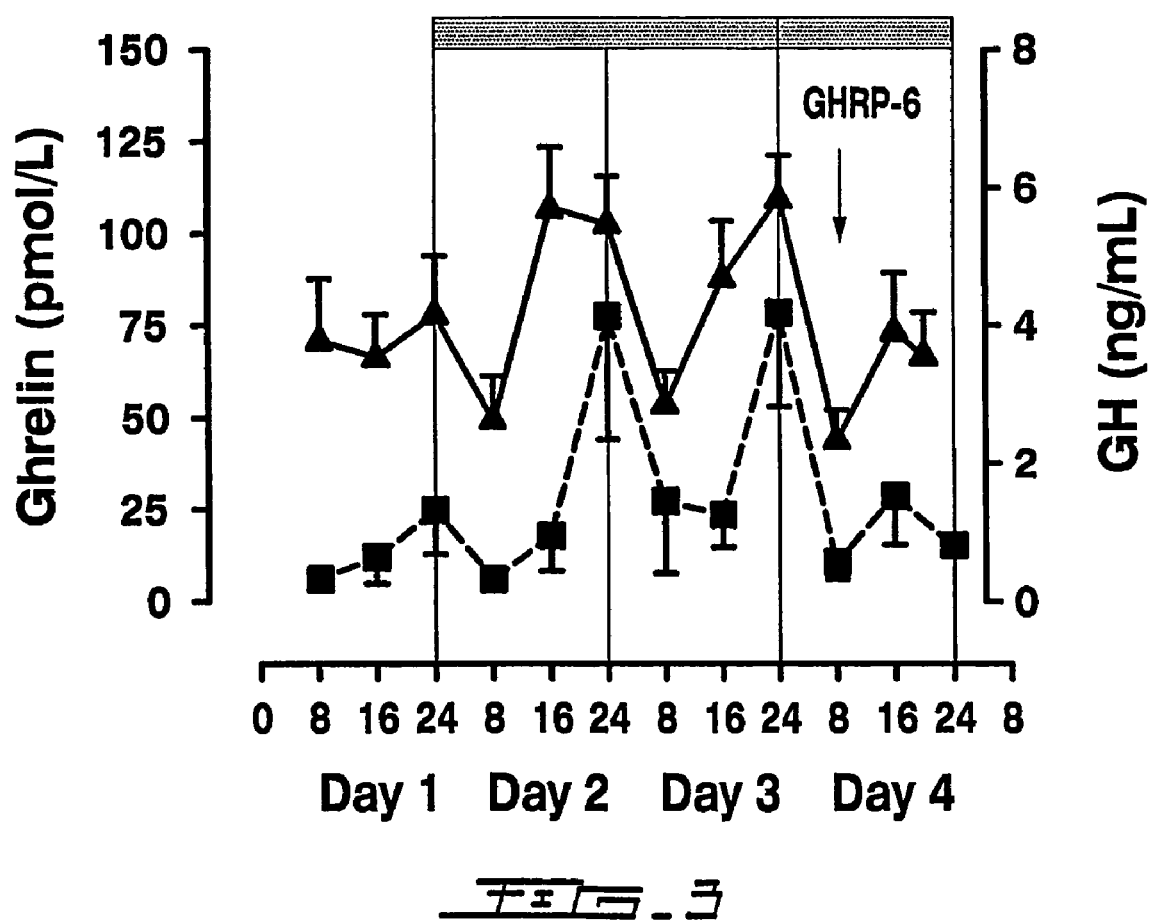
FIG. 3 illustrates the serum Ghrelin, and GH concentrations (Solid line: ghrelin levels; dotted line: GH levels) during fasting for three days and after a bolus injection of GHRP-6 on day 4.

In order to understand the diurnal rhythms of ghrelin and GH secretion during fasting, a study was conducted on 10 healthy human volunteers with normal body mass index. FIG. 3 shows the serum Ghrelin, and GH concentrations (Solid line: ghrelin levels; dotted line: GH levels). during fasting for three days and after a bolus injection of GHRP-6 on day 4. Fasting rapidly induces a diurnal ghrelin rhythm that is followed by a similar GH rhythm. Administration of 1 μg/kg of GHRP-6 on the 3rd day of fasting attenuated peak ghrelin levels in the afternoon. This clearly shows that fasting induces an acute and distinct diurnal rhythm in systemic ghrelin concentrations that is not present in the fed state. These changes in serum ghrelin levels during fasting are followed by similar changes in serum GH concentrations, indicating that ghrelin is the driving force of increased GH secretion during fasting. This phenomenon cannot be explained by changes in insulin, glucose or free fatty acid levels. Thus it appears that the metabolic effects of ghrelin are distinct from its effects on GH secretion.

By the use of the GH receptor antagonist pegvisomant, indirect evidence was provided that these changes in serum ghrelin levels are not regulated by the GH receptor. Finally, it was shown that administration of the synthetic GHS, GHRP-6, produced a decrease in peak ghrelin levels, but this effect was only observed after several hours, indicating the existence of a long-loop feedback system of GHS's on ghrelin secretion.

Figure 4A:
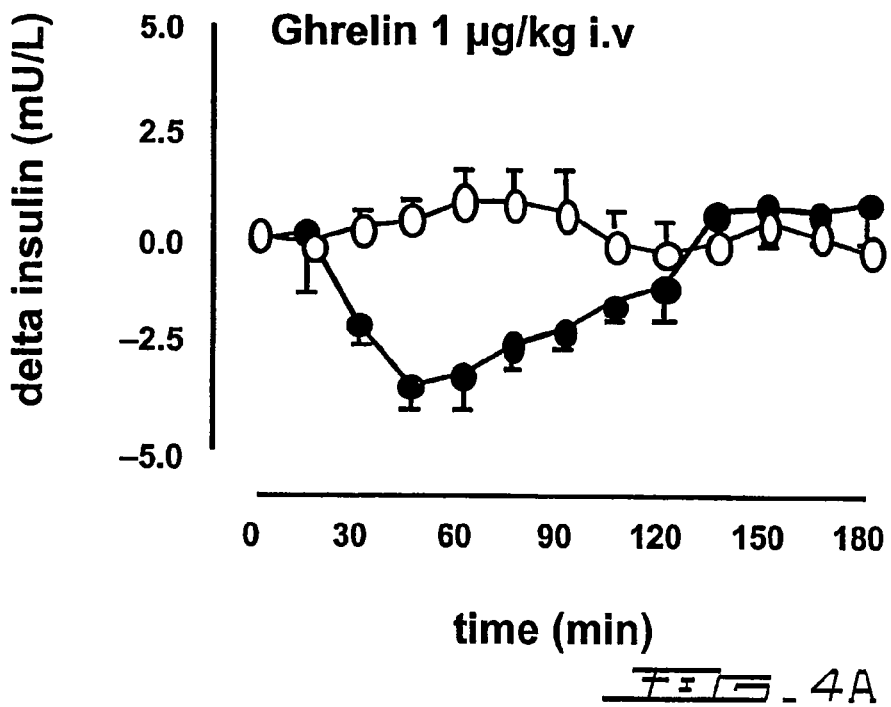
FIG. 4A illustrates insulin variation over time in a patient having received a single intravenous administration of human ghrelin (solid dots) or placebo (open dots)
Figure 4B:
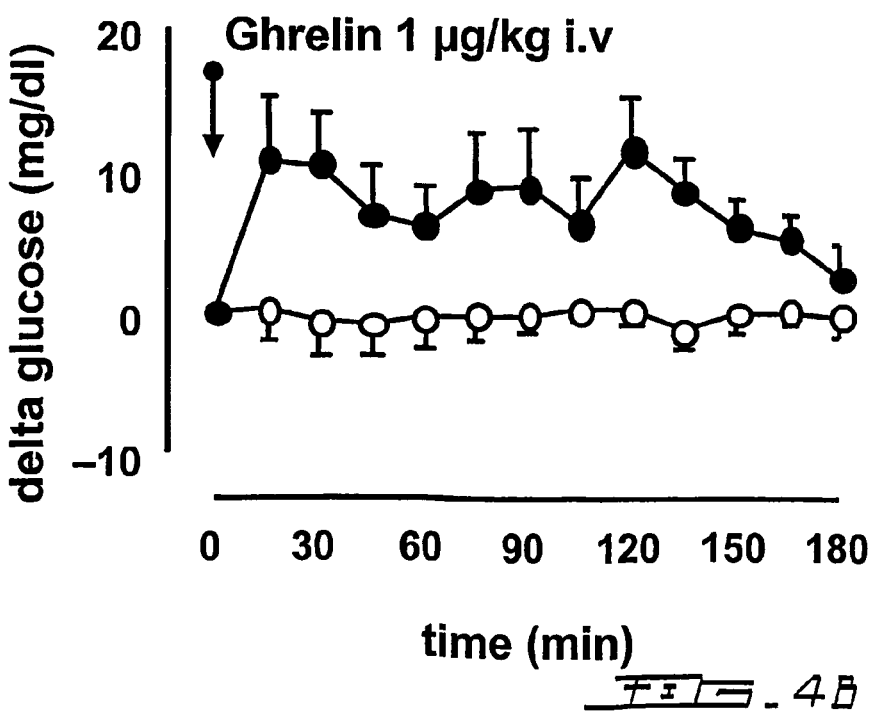
FIG. 4B illustrates glucose variation over time in a patient having received a single intravenous administration of human ghrelin (solid dots) or placebo (open dots)

In order to elucidate the metabolic effects of ghrelin, a study was performed on 11 healthy young male volunteers in whom glucose and insulin levels were measured after a single intravenous administration of human ghrelin (1.0 μg/kg i.v. at 0') or placebo. FIG. 4 shows that ghrelin produced acute decrease in insulin [mean (±SEM) Δ insulin] (top panel) and elevation in glucose [Δ mean (±SEM) glucose] levels (bottom panel) (solid dots: ghrelin; open dots: placebo). This data clearly shows that ghrelin has distinct and immediate effects on glucose and insulin, two important determinants of metabolism in humans (Broglio F et al. *Journal of Clinical Endocrinology & Metabolism* 2001; 86(10):5083-5086).

Thus the data reported in the present application, indicate that ghrelin has important physiological actions, not only on GH secretion but also on the modification of glucose and insulin concentrations in living (human or animal) beings.

Ghrelin appears to have a role in managing not only GH secretion but also the metabolic response to starvation by modulating insulin secretion and glucose metabolism.

In an analysis of a study in normal human volunteers (n=6), it was surprisingly observed that the administration of unacylated ghrelin (1 μg/kg iv at 0 min) totally prevented the ghrelin (1 μg/kg iv at 0 min)-induced increase in glucose and decrease in insulin levels. The lots of unacylated ghrelin used in this study had the following specifications: tifluoroacetate salt of unacylated ghrelin, 95.1% pure as judged by HPLC, Mass: 3244.7 amu, and the peptide has amino acid composition representative of the sequence listed in SEQ ID. NO:. 1.

Figure 5A:
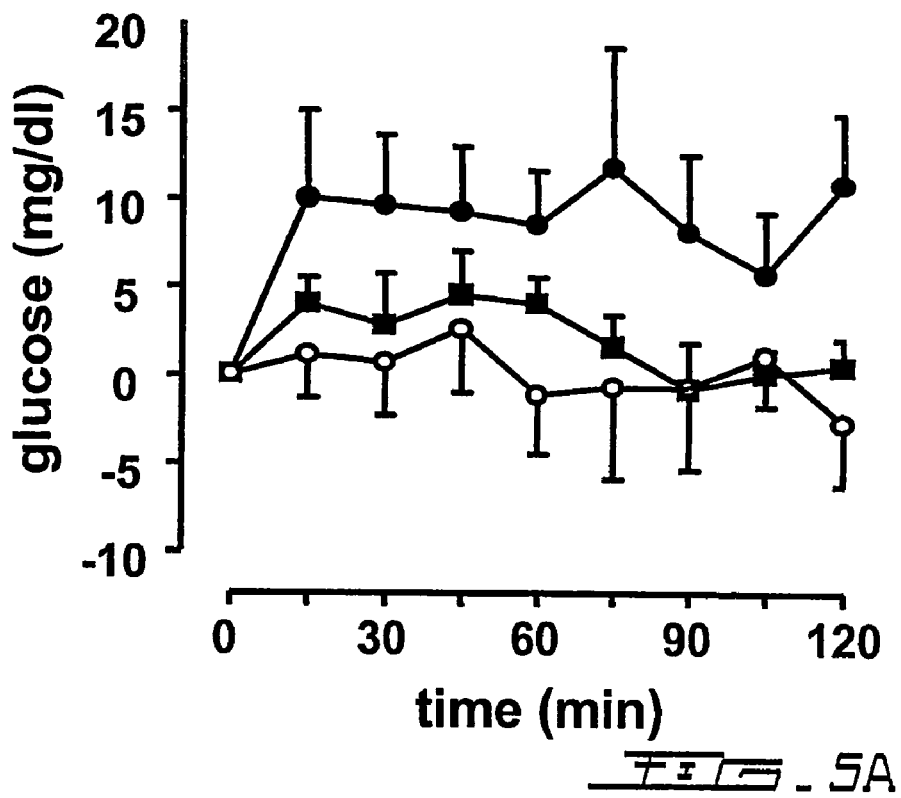
FIG. 5A illustrates insulin level over time in a patient having been administered with ghrelin, desoct-ghrelin or ghrelin and desoct-ghrelin.
Figure 5B:
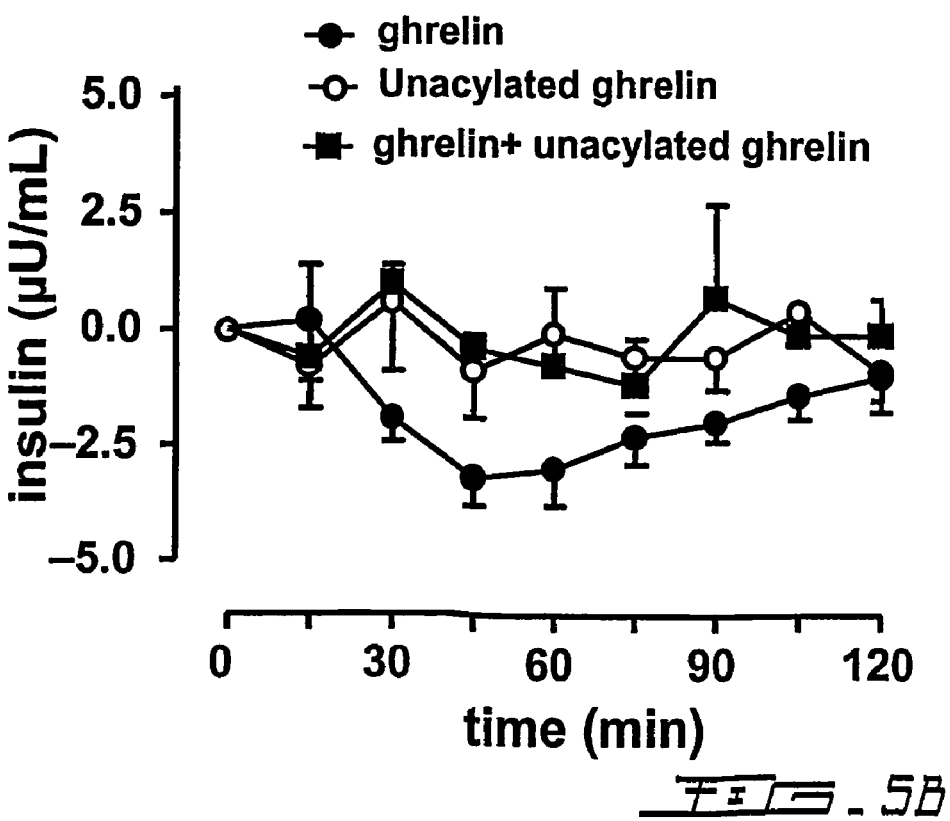
FIG. 5B illustrates glucose level over time in a patient having been administered with ghrelin, desoct-ghrelin or ghrelin and desoct-ghrelin.

FIGS. 5A-5B show the mean (±SEM) Δ insulin (top panel) and Δ glucose (bottom panel) levels after a single intravenous administration of human acylated ghrelin (1.0 μg/kg i.v. at 0'), human des-acylated ghrelin (1.0 μg/kg i.v. at 0') or the co-administration of both. Thus it appears that unacylated ghrelin is acting as a functional antagonist of the peripheral actions of ghrelin. This last result was surprising and unexpected, since unacylated ghrelin has never been shown previously to antagonize or inhibit the biological effects of acylated ghrelin. Most of ghrelin actions, especially on GH secretion were thought to be mediated by GHS-R1a receptor for which unacylated ghrelin has little affinity. In fact, unacylated ghrelin has so far been considered as a peptide without any biological activity.

Hence in this invention, it was shown that unacylated ghrelin acts as a functional antagonist to inhibit important peripheral actions of acylated ghrelin on two crucial parameters of metabolism-insulin and glucose. To provide therapeutic benefits to patients in various states of insulin resistance, preferably those associated with low GH action and/or increased acylated ghrelin secretion, unacylated ghrelin (NH$_2$Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg: SEQ ID NO. 1) or its analogue may be administred in a pharmaceutical composition intravenously, subcutaneously, transdermally, orally or by inhalation. Preparation of pharmaceutical compositions suitable for intravenous, subcutaneous, transdermal, oral, buccal, sublingual and pulmonary delivery are known to people skilled in the arts.

It is understood that the data reported in the present specification are only given to illustrate the invention and may not be regarded as constituting a limitation thereof.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for lowering elevated blood glucose in a patient comprising administering to said patient a therapeutically effective amount of an agent selected from the group consisting of (a) unacylated ghrelin; (b) the unacylated ghrelin of (a) having one or more conservative amino acid substitutions; and (c) pharmaceutically acceptable salts of (a) and (b).

2. The method of claim 1, wherein the elevated blood glucose is associated with insulin resistance.

3. The method of claim 1, wherein the elevated blood glucose is associated with insulin deficiency.

4. The method of claim 1, wherein the agent antagonizes acylated ghrelin.

5. The method of claim 1, wherein said agent is administered through a route selected from the group consisting of intravenous, subcutaneous, transdermal, oral, buccal, sublingual, nasal and inhalation.

6. The method of claim 1, wherein said agent is administered in a dose varying from about 0.001 µg/kg to 10.0 µg/kg.

7. The method of claim 1, wherein said agent is administered in a dose varying from about 1 µg/kg to 1 mg/kg.

8. The method of claim 1, wherein the elevated blood glucose is associated with a postprandial insulin resistance.

9. The method of claim 1, wherein the elevated blood glucose is associated with a body weight increase in a patient suffering from a condition selected from the group consisting of type II diabetes and syndrome X.

10. The method of claim 1, wherein said unacylated ghrelin comprises the amino acid sequence set forth in SEQ ID NO: 1.

11. The method of claim 1, wherein the unacylated ghrelin having one or more conservative amino acid substitutions is naturally-occurring.

12. A method for modulating and/or treating insulin resistance in a patient comprising administering to said patient a therapeutically effective amount of an agent selected from the group consisting of (a) unacylated ghrelin; (b) the unacylated ghrelin of (a) having one or more conservative amino acid substitutions; and (c) pharmaceutically acceptable salts of (a) and (b).

13. The method of claim 12, wherein said agent is administered through a route selected from the group consisting of intravenous, subcutaneous, transdermal, oral, buccal, sublingual, nasal and inhalation.

14. The method of claim 12, wherein said agent is administered in a dose varying from about 0.001 µg/kg to 10.0 µg/kg.

15. The method of claim 12, wherein said agent is administered in a dose varying from about 1 µg/kg to 1 mg/kg.

16. The method of claim 12, wherein said patient is in severe catabolism.

17. The method of claim 12, wherein the patient suffers from type II diabetes.

18. The method of claim 12, wherein the insulin resistance is associated with low growth hormone action.

19. The method of claim 12, wherein the insulin resistance is postprandial.

20. The method of claim 12, wherein said unacylated ghrelin comprises the amino acid sequence set forth in SEQ ID NO: 1.

21. The method of claim 12, wherein the unacylated ghrelin having one or more conservative amino acid substitutions is naturally-occurring.

* * * * *

UNITED STATES PATENT AND TRADEMARK OFFICE
CERTIFICATE OF CORRECTION

PATENT NO. : 7,485,620 B2
APPLICATION NO. : 10/499376
DATED : February 3, 2009
INVENTOR(S) : Ezio Ghigo et al.

It is certified that error appears in the above-identified patent and that said Letters Patent is hereby corrected as shown below:

In Column 4, Line 7, delete "patent;" and insert -- patient; --, therefor.

In Column 4, Line 15, delete "patent;" and insert -- patient; --, therefor.

In Column 4, Line 30, delete "patent;" and insert -- patient; --, therefor.

In Column 4, Line 33, delete "patent;" and insert -- patient; --, therefor.

In Column 4, Line 50, delete "patent;" and insert -- patient; --, therefor.

In Column 5, Line 36, delete "des-gln14ghrelin;" and insert -- des-gln14-ghrelin; --, therefor.

Signed and Sealed this

Fourth Day of August, 2009

JOHN DOLL
*Acting Director of the United States Patent and Trademark Office*